(12) United States Patent
Alzahrani et al.

(10) Patent No.: US 8,703,205 B2
(45) Date of Patent: Apr. 22, 2014

(54) NATURAL COMPOSITIONS AND METHODS OF PROMOTING WOUND HEALING

(76) Inventors: Hasan Ali Alzahrani, Jeddah (SA); Balkees Abed Bakhotmah, Jeddah (SA)

( * ) Notice: Subject to any disclaimer, the term of this patent is extended or adjusted under 35 U.S.C. 154(b) by 340 days.

(21) Appl. No.: 13/198,025

(22) Filed: Aug. 4, 2011

(65) Prior Publication Data

US 2013/0034529 A1 Feb. 7, 2013

(51) Int. Cl.
*A61K 35/64* (2006.01)
*A61K 36/328* (2006.01)
*A61K 36/00* (2006.01)

(52) U.S. Cl.
USPC .................. 424/537; 424/748; 424/725

(58) Field of Classification Search
USPC ......................... 424/537, 748, 725
See application file for complete search history.

(56) References Cited

U.S. PATENT DOCUMENTS

| | | |
|---|---|---|
| 6,482,442 B1 | 11/2002 | Dado |
| 2003/0060508 A1* | 3/2003 | Kandil .................. 514/560 |
| 2006/0070189 A1 | 4/2006 | Raehse et al. |
| 2007/0134195 A1* | 6/2007 | Ward et al. .................. 424/74 |
| 2008/0050500 A1 | 2/2008 | Muranishi et al. |
| 2008/0125617 A1* | 5/2008 | Puchek .................. 600/14 |
| 2009/0035337 A1 | 2/2009 | Artiga-Gonzalez et al. |
| 2010/0022437 A1 | 1/2010 | Artiga-Gonzalez et al. |

OTHER PUBLICATIONS

Lebling, et al, Natural Remedies of Arabia (excerpt), Saudi Aramco World, vol. 57, No. 5, Sep./Oct. 2006, 15 pages.
Mark, et al., The Middle East: exploring the virtues of traditional Arabic Medicine, Nutraceuticals World, 11.10, Nov. 2008, 3 pages.
The University of Waikato, Honey as an Antimicrobial Agent, Waikato Honey Research Unit (2006), retrieved Sep. 16, 2010, 13 pages.
Author Pandita Narahari, Title of publication—Rajanighantauh, Page(s) being submitted—05(p. no. 04-08), (Ref. p. No. of publication:498), Publication Date—1998, Publisher—Krishnadas Academy, Place of Publication—Varanasi, India.
Author Madhavah, Title of publication—Ayurvedaprakasah, Page(s) being submitted—05 (p. No. 09-13) (Ref. p. No. of publication:333), Publication Date—1999, Publisher—Chaukhamba Bharati Academy, Place of Publication—Varanasi, India.
Author Mohammad Azam Khan, Title of publication—Muheet-e-Azam vol. III, Page(s) being submitted—04 (p. No. 14- 17) (Ref. p. No. of publication:143), Publication Date—1887, Publisher—Matba Nizami, Place of Publication—Kanpur, India.

\* cited by examiner

*Primary Examiner* — Rosanne Kosson
(74) *Attorney, Agent, or Firm* — Bacon & Thomas, PLLC

(57) ABSTRACT

Compositions comprising honey, myrrh, and *Nigella Sativa* seeds are described. The honey:myrrh:*N. sativa* seed ratio can be 100:0.5-50:0.1-10, based on weight. The compositions can also comprise one or more pharmaceutically acceptable diluents and/or excipients. Also described herein are methods for treating a wound comprising administering to the wound an effective amount of the present composition. The wound can be a bed sore or a diabetic ulcer. The wound can also be infected.

12 Claims, No Drawings

NATURAL COMPOSITIONS AND METHODS OF PROMOTING WOUND HEALING

FIELD

The present application is generally directed to the field of medicine and pharmacology, particularly to compositions comprising honey, myrrh, and black seeds, and uses thereof for the treatment of wounds.

BACKGROUND

A variety of natural products are available for treating many diseases and conditions affecting the human body. Natural preparations for treating wounds may be less likely to have an adverse effect on the body compared to synthetic preparations.

While primary damage may be inflicted by different causes, the healing of skin ulcers, traumatic wounds, burns and other open skin wounds and injuries usually undergo similar sequence of steps that results in restoration of structural integrity of the skin. These steps include wound cleansing, achieved through the influx of inflammatory cell, proliferation of stromal cells to initiate the restorative processes and ingrowth of blood vessels to provide nutritional support for the regeneration. Effective treatment may be expected to promote wound healing through the support of these steps and protection of the area of open injury against bacterial infection and dehydration.

In spite of considerable advances in recent years in the treatment of wounds, the occurrence of bedsores or decubitus ulcers continues to grow. Increases in the number of diabetic patients and patients with restricted mobility, which most frequently suffer from bedsores and ulcers, calls for the introduction of new, more efficient, and safe treatments. There are many different products available for the treatment of bedsores and ulcers, mostly addressing the issues of prevention and elimination of bacterial infection and protection against dehydration. Medications with potent antibacterial agents, such as antibiotics, iodine derivatives, hydrogen peroxide, boric acid derivatives etc. are good in protecting against infection, but the occurrence of allergic reactions and skin irritations to these agents may further reduce the rate of skin regeneration, thus increasing recovery time. Medications comprising synthetic antibacterial agents, hormones, or hormone derivatives, often induce skin sensitization during repetitive applications, usually required for successful treatment. Administration of such medications on a daily basis may cause increasing skin irritation and inflammatory response, interfering with the healing process. There is a need for new pharmaceutical compositions derived from natural sources suitable for the treatment of wounds.

SUMMARY

Described herein are compositions comprising honey, myrrh, and *Nigella Sativa* seeds. In certain embodiments, the honey:myrrh:*N. sativa* seed ratio is 100:0.5-50:0.1-10, based on weight. The compositions can also comprise one or more pharmaceutically acceptable diluents and/or excipients.

Also described herein are methods for treating a wound in a subject in need thereof, comprising administering to the wound an effective amount of the present composition. In certain embodiments, the wound is a bed sore or a diabetic ulcer. The wound can also be infected.

DETAILED DESCRIPTION

The present application describes novel compositions comprising honey, myrrh, and *N. sativa* seeds, and medicinal uses thereof. The composition may further comprise one or more pharmaceutically acceptable carrier and/or vehicle.

Honey is a sweet food made by bees using nectar from flowers. The variety produced by honey bees (the genus *Apis*) is the one most commonly referred to and is the type of honey collected by beekeepers and used by humans. Honey bees form nectar into honey by a process of regurgitation and store it as a primary food source in wax honeycombs inside the beehive.

Honey gets its sweetness from the monosaccharides fructose and glucose and has approximately the same relative sweetness as that of granulated sugar. Honey has a long history of human consumption and is used in various foods and beverages as a sweetener and flavoring. It is also used in various medicinal traditions to treat numerous ailments. Most microorganisms do not grow in honey, at least in part because of its low water activity (aw) of about 0.6, acidic pH of about 3.2 to 4.5, and hydrogen peroxide content. In particular, honey is known to have antibacterial and antifungal activity against a broad spectrum of bacterial and fungal species.

Besides sugar, honey may also contain enzymes such as invertase, diastase, catalase, amylase, phosphatase, and glucose oxidase; organic acids such as malic acid, succinic acid, gluconic acid, acidic acid, and formic acid; inorganic acids such as phosphoric acid and hydrochloric acid; minerals such as Fe, Cu, P, S, K, Na, Mg, Ca, Si, Mn, Cl, and Zn; and, in small amounts, vitamins such as B1, B2, B6, pantothenic acid, nicotinic acid, H, folic acid, and vitamin C.

Myrrh is a gum resin extracted from the stems of certain plants found growing mainly in southern Arabia and Somolia. Myrrh is also sometimes referred to as myrrha, mine, myrrhis, gummi myrrha, myrrha vera, gum myrrh, *Commiphora* resin, gruggal gum, gruggal resin, Herabol myrrh, myrrhe, Manniliche myrrhe, Opopanax, and Hirabol myrrh. Myrrh can comprise gum resin obtained from cuts made in the bark of trees of the genus *Commiphora* (also sometimes referred to as "Commophora"), i.e. the myrrh tree. Myrrh can also comprise balsamic juices from Balsamodendron myrrha, a buraceous tree. Myrrh can also be extracted from Osmorhiza or Washingtonia, which is also sometimes referred to as sweet cicely.

The myrrh-producing *Commiphora* species are shrubs or small trees with large, sharply pointed thorns on the stem. When damaged, the schizogenous resin ducts yield the drug myrrh. There are different types of *Commiphora*, such as *Commiphora molmol, Commiphora myrrha, Commiphora erythraea*, and their cultivars. There is considerable confusion in the literature regarding the sources of myrrh and the identity of the *Commiphora* species involved. Common (or hirabol) myrrh appears to derive from *Commiphora myrrha*. Somalian myrrh is said to come from *Commiphora molmol*. However, the systematic (taxonomic) relationship between *Commiphora myrrha* and *Commiphora molmol* is not clear. The source of Abyssinian myrrh is *Commiphora madagascariensis* or *Commiphora abyssinica*. Opopanax, which is also referred to as bisabol myrrh or perfumed bdellium is believed to originate from either *Commiphora erythraea* (Ehrenb) or Opopanax.

Myrrh has many recognized medicinal benefits, including anti-catarrhal, anti-inflammatory, antimicrobial, antiseptic, astringent, balsamic, carminative, cicatrisant, emmenagogue, expectorant, fungicidal, sedative, digestive, stomachic, tonic, and vulnerary properties. Myrrh is known to be useful externally as a topical preparation to help treat infected wounds, minor skin inflammations, and sores such as skin ulcers and bedsores.

Myrrh is generally in the form of an air-dried oleo-gum resin that exudes from the bark of *Commiphora* species. In chloral-hydrate mounts, there are only a few fragments of tissue from the plant source. The composition of myrrh is very complex and only partially known. Generally from 40-60% of myrrh is soluble in ethanol and comprises a resin and an essential oil. Myrrh may contain polysaccharides, triterpenoids, triterpene acids and an essential oil containing sesquiterpenes and furano sesquiterpenes. The main components of sesquiterpenes are furanosesquiterpenes of the germacrane elemane, eudesmane, and guaiane types. In addition, there are sesquiterpene hydrocarbons, and sesquiterpene alcohols, e.g. elemol.

In the present compositions, the myrrh may be in the form of a powder. The myrrh powder can be prepared by grinding myrrh using a mill. For example, the resulting myrrh powder may have an average grain size of from about 1 mm to about 2 mm (i.e. very coarse size sand or ϕ scale 0-1).

*Nigella sativa* seeds come from an herbaceous plant that belongs to the Ranunculaceae family. The seeds are commonly known as black seed or black curcumin, and may also be referred to as as habbatul baraka (meaning the seed of good fortune) in the Mediterranean region, and kalajira or kalaoji or black cumin in the Indian subcontinent. The plant is cultivated in various parts of the world, especially in Eastern Mediterranean countries and also in India, Bangladesh, Turkey and Pakistan. It is also grown in other places having similar climates, such as East Africa, North Africa and the Middle East.

*N. sativa* seeds have been traditionally used for culinary purposes as a spice and a condiment, and for medicinal purposes as a natural remedy for a number of illnesses and conditions that include asthma, hypertension, diabetes, inflammation, cough, headache, and fever. Among the physiological effects studied include antioxidant effects, anti-inflammatory and analgesic actions, anticarcinogenic activity, hypotensive effects, antidiabetic, antiulcer, antimicrobial and antiparasitic actions (see, e.g., Ali and Blunden, 2003, Pharmacological and toxicological properties of *Nigella sativa*, Phytother Res 17: 299-305).

*N. sativa* seeds generally contain 36-38% fixed oils, proteins, alkaloids, saponin and 0.4-2.5% essential oil. The fixed oil is composed mainly of unsaturated fatty acids, including the unusual C20:2 arachidic and eiosadienoic acids. Major components of the essential oil include thymoquinone (27-57%), p-cymene (7.1-15.5%), carvacrol (5.8-11.6%), trans-anethole (0.25-2.3%) p-terpineol (2.0-6.6%) and longifoline (1.0-8.0%).

In the present compositions, the *N. sativa* seeds are in the form of a powder. The *N. sativa* seed powder can be prepared by grinding *N. sativa* seeds using a mill. For example, the resulting *N. sativa* seed powder may have an average grain size of from about 125 mm to about 250 µm (i.e. fine size sand or ϕ scale 3-2).

In certain embodiments, the present composition comprises honey, myrrh, and *N. sativa* seeds at a honey:myrrh:*N. sativa* seed ratio of 100:0.5-50:0.1-10, based on weight. In certain embodiments, the honey:myrrh:*N. sativa* seed ratio is 100:1-25:0.2-5, 100:2-20:0.5-2.5, 100:5-15:1-1.5, 100:5-10: 1-1.5, 100:5-9:1-1.5, 100:5-8:1-1.5, or 100:5-7:1-1.5, 100:6-7:1-1.5, based on weight. Specific examples are honey:myrrh:*N. sativa* seed ratios of 100:3.42:1.25, 100:5.13:1.25, 100:6.84:1.25, and 100:3.42:2.50, based on weight.

Described herein are methods for treating wounds in a patient in need thereof by administering a therapeutically effective amount of the present composition. The compositions of the present invention can be administered topically, orally, parenterally, by inhalation (nasal or oral), vaginally, or rectally in dosage unit formulations containing conventional nontoxic pharmaceutically acceptable carriers, adjuvants, and vehicles, as desired. The term parenteral as used herein includes subcutaneous, intravenous, intramuscular, intrasternal injection, or infusion techniques.

The present composition can be formulated with only honey, myrrh, and *N. sativa* seeds. Alternatively, one or more pharmaceutically acceptable diluents, excipients or carriers can be added. For example, the composition can comprise a sterile aqueous solution to give a range of final concentrations depending on the intended use. Furthermore, the composition may comprise substances which assist in its application or storage stability, such as, e.g., stabilizers, preservatives, pharmaceutical adjuvants, water, buffer substances, thickening agents, emulsifiers, and the like. The techniques of preparing pharmaceutical compositions are generally well known in the art as exemplified by Remington's Pharmaceutical Sciences, 16th Ed. Mack Publishing Company, 1980. Moreover, for human administration, preparations should meet sterility, pyrogenicity, and general safety and purity standards, e.g. as required by the FDA Office of Biological Standards.

In certain embodiments, the compositions are topically administered. "Topical" administration here means local, external administration to a wound. The composition may be topically administered directly to all or to part of the wound or peripherally to the wound. Topical administration includes administration to the vulva and vagina.

For topical administration, for example, the compositions can be formulated as a gel, ointment, cream, balm, or lotion. Topical administration can also be accomplished with a liquid spray, an aerosol, or via iontophoresis, or through the use of liposomes, microbubbles and/or microcapsules. A composition suitable for topical administration can be formulated with only honey, *N. sativa* seeds, and myrrh. Alternatively, one or more pharmaceutically acceptable excipients and/or carriers can be added.

Gels, ointments and creams may be formulated, for example, with an aqueous or oily base with the addition of suitable thickening (e.g., wax, beeswax, PEG 4000, PEG 600, hard paraffin) and/or gelling agents (e.g., hydroxypropyl cellulose). Lotions may be formulated with an aqueous or oily base and can also generally contain one or more emulsifying agents (e.g., wool wax alcohol, fatty acid glycol esters), stabilizing agents (e.g., polyoxyethylene sorbitan monolaurate, carboxy methyl cellulose), dispersing agents (e.g., sodium oleate, propylene glycol), suspending agents (e.g., methyl cellulose, chitosan, accacia, carboxymethyl cellulose, tragacanth, pectin), thickening agents, and/or coloring agents (e.g., dyes, lackes). Other conventional pharmaceutical excipients for topical application include pluronic gels, polaxamer gels, hydrogels containing cellulose derivatives, including hydroxyethyl cellulose, hydroxymethyl cellulose, carboxymethyl cellulose, hydroxypropylmethyl cellulose and mixtures thereof; and hydrogels containing polyacrylic acid (carbopols). Suitable carriers also include creams/ointments conventionally used for topical pharmaceutical preparations, e.g., creams based on cetomacrogol emulsifying ointment. The above carriers may include alginate (as a thickener or stimulant), preservatives such as benzyl alcohol, buffers to control pH such as disodium hydrogen phosphate/sodium dihydrogen phosphate, agents to adjust osmolarity such as sodium chloride, and stabilizers such as EDTA.

In certain embodiments, the present composition comprises wax in an amount ranging from 1-50% by weight based on 100% by weight of the total composition, such as 5-40%, 10-30%, 15-25%, or 20% by weight based on 100% by weight of the total composition. Any pharmaceutically acceptable wax can be used. In certain embodiments, the wax is bees wax.

The composition can be applied directly to the wound as a gel, ointment, liquid, cream, or the like as described above. Alternatively, the composition is administered in the form of a wound dressing. As used herein, the terms "wound dressing" and "dressing" refer broadly to any substrate when prepared for, and applied to, a wound for protection, absorbance, drainage, etc., and may include any one of the numerous types of substrates and/or backings that are commercially available, including films (e.g., polyurethane films), hydrocolloids (hydrophilic colloidal particles bound to polyurethane foam), hydrogels (cross-linked polymers containing about at least 60% water), foams (hydrophilic or hydrophobic), calcium alginates (non-woven composites of fibers from calcium alginate), and cellophane (cellulose with a plasticizer). For example, the composition can be applied to the surface of, or incorporated into, a solid contacting layer such as a dressing gauze or matrix. Suitable gauze dressings may include, for example, dry woven or non-woven sponges, swabs, bandages and wraps with varying degrees of absorbency. Exemplary fabric composition may include, for example, cotton, polyester or rayon. In certain embodiments, gauzes and non-woven dressings may be available sterile or non-sterile in bulk and with or without an adhesive border. In certain embodiments the dressings also comprise one or more additional pharmaceutically active compound and/or carrier agent, including for example, saline, oil, zinc salts, petrolatum, xeroform and scarlet red.

While the compositions can be administered with honey, myrrh, and N. sativa seeds as the only active pharmaceutical agents in the methods described herein, they can also be used in combination with one or more compounds which are known to be therapeutically effective for wound treatment.

The present composition and/or the components of the composition may be sterilized by any suitable method, including conventional, well known sterilization techniques, such as autoclaving. Raw, unheated honey can be sterilized, for example, by ozonizing the honey using an ozone generator (see Vandeputte, U.S. Patent Application Publication No. 2010/0028408).

The dosage regimen for treating wounds is selected in accordance with a variety of factors, including the age, weight, sex, and medical condition of the patient, the severity of the wound, the route of administration, pharmacological considerations such as the activity, efficacy, pharmacokinetic and toxicology profiles of the particular composition used, whether a dressing or drug delivery system is used and whether the composition is administered as part of a drug combination.

The doses may be administered in single or divided applications. The doses may be administered once, or application may be repeated. Application may be repeated weekly until wound healing is promoted, or a repeat application may be made in the event that wound healing slows or is stalled. Doses may be applied 1-7 days apart, or more. In the case of a chronic wound, repeat applications may be made, for example, one or more times per day, weekly, or bi-weekly, or monthly or in other frequency for example if and when wound healing slows or is stalled. For some indications more frequent dosing such as hourly application may be employed. The composition may be administered before, during, immediately following wounding, or later, for example when infection is diagnosed.

"Treatment" or "treating," as used herein, refers to complete elimination as well as to any clinically or quantitatively measurable healing of the wound. Treatment may include, for example, promoting or accelerating wound healing, wound closure, and/or wound repair; reducing infection; reducing swelling and inflammation; and/or minimizing scar formation.

A "therapeutically effective amount" means the amount of a composition that, when administered to a subject for treating a wound, is sufficient to effect a desirable treatment for the wound. The "therapeutically effective amount" will vary depending on the particular composition, the wound and its type and severity, and the age, weight, etc., of the subject to be treated. A "therapeutically effective amount" need not result in a complete cure, but may provide partial relief of one or more symptoms or retard the progression of a condition such as infection.

"Patient" or "subject" refers to animals, and can include any mammal, such as human beings, rats, mice, cats, dogs, goats, sheep, horses, monkeys, apes, rabbits, cattle, etc. The mammalian subject can be in any stage of development including adults, children, infants, and neonates.

As used herein, the term "wound" includes an injury to any tissue, including, for example, acute, delayed or difficult to heal wounds, chronic wounds, and infected wounds. The term "wound" includes injuries to the skin and subcutaneous tissue initiated in different ways (e.g., pressure sores from extended bed rest and wounds induced by trauma) and with varying characteristics. The wounds amenable to treatment by the composition include injuries that can be located in any site, including external, interfacial, interstitial, extracorporeal, and/or intracorporeal. Also included are wounds that do not heal at expected rates. Examples of wounds may include both open and closed wounds. Wounds include, for example, cuts, gashes, lacerations, lesions, incisions, excisions, abrasions, surgical wounds, contusions, hematoma, crushing injuries, tissue rupture, Decubitus, Dermatitis, acute wounds, chronic wounds, battlefield wounds, necrotic wounds, necrotizing facitis, toxic epidermal nercolysis, pressure wounds, venous insufficiency ulcers, arterial ulcers, diabetic or neuropathic ulcers, pressure ulcers, mixed ulcers, burn wounds, Mucormycosis, Vasculitic wounds, Pyoderma, gangrenosum, and equivalents, and/or combinations thereof, known by persons skilled in the art.

Examples of wounds that do not heal at the expected rate can include ulcers such as diabetic ulcers, diabetic foot ulcers, vascultic ulcers, arterial ulcers, venous ulcers, venous stasis ulcers, burn ulcers, infectious ulcers, trauma-induced ulcers, pressure ulcers, decubitus ulcers, ulcerations associated with pyoderma gangrenosum, and mixed ulcers. Other wounds that do not heal at expected rates include dehiscent wounds. A delayed or difficult to heal wound may include, for, example, a wound that is characterized at least in part by a prolonged inflammatory phase, a slow forming extracellular matrix, and/or a decreased rate of epithelialization or closure.

In certain embodiments the wound is infected with one or more of the following microorganisms: Staphylococcus aureus, Enterococcus faecalis, Pseudomonas aeruginosa, Escherichia coli, Candida albicans, Proteus mirabilis, Streptococcus pyogenes, Morganella morganii, Streptococcus pyogenes, Methicillin-resistant Staphylococcus aureus (MRSA), Vancomycin-resistant Enterococcus (VRE).

MRSA is a bacterium responsible for several difficult-to-treat infections in humans. It may also be called multidrug-resistant Staphylococcus aureus or oxacillin-resistant Staphylococcus aureus (ORSA). MRSA is, by definition, any strain of Staphylococcus aureus bacteria that has developed resistance to beta-lactam antibiotics which include the penicillins (methicillin, dicloxacillin, nafcillin, oxacillin, etc.)

and the cephalosporins. MRSA is especially troublesome in hospitals or other health care settings, such as nursing homes and dialysis centers, where patients with open wounds, invasive devices and weakened immune systems are at greater risk of infection than the general public. VRE refers to several different species of antibiotic resistant *Enterococcus* bacteria that share similar characteristics and background. Similar to MRSA, people who are most susceptible for VRE infection are those in health care settings and/or with weakened immune systems.

As used herein, the singular forms "a", "an" and "the" include plural referents unless the context clearly dictates otherwise.

The publications disclosed herein are provided solely for their disclosure prior to the filing date of the present application. Nothing herein should be construed as an admission that the present disclosure is not entitled to antedate such publication by virtue of prior disclosure. Further, the dates of publication provided may be different from the actual publication dates, which may need to be independently confirmed. All publications, patents, patent applications and other references cited herein are hereby incorporated by reference in their entirety.

While the disclosure has been described in detail with reference to certain embodiments thereof, it will be apparent to one skilled in the art that various changes can be made, and equivalents employed, without departing from the scope of the disclosure. In addition, the following examples are illustrative only and should not be considered as limiting the disclosure in any way.

EXAMPLES

Example 1

Effect of Six Natural Preparations on Certain Bacterial Strains

A microbiological laboratory study carried out as a controlled, blind, comparative study on 5 strains of organisms commonly seen in diabetic foot ulcers (*Staphylococcus aureus, Enterococcus faecalis, Pseudomonas aeruginosa, Escherichia coli, Candida albicans*), using 6 natural preparations (NPs) comprising various combinations of honey (H), myrrh (M), and/or black seeds (B) applied on each bacterial strain. The 6 NPs were compared to two topical dressing agents (MEBO™, FUCIDIN™) and two standard antibiotics which are commonly used in treating diabetic foot infections (Ciprofloxacylline, Clindamycine).

List of the 10 agents used:
 0.100 g honey, 0 g myrrh, and 0 g black seed
 1.100 g honey, 1.25 g myrrh, and 0 g black seed
 2.100 g honey, 1.25 g myrrh, and 1.71 g black seed
 3. 100 g honey, 2.5 g myrrh, and 1.71 g black seed
 4. 100 g honey, 3.75 g myrrh, and 1.71 g black seed
 5. 100 g honey, 5.0 g myrrh, and 1.71 g black seed
 6. MEBO™
 7. FUCIDIN™
 8. Ciprofloxacylin
 9. Clindamycin Natural Preparations (NPs) Six NPs (NPs 0-5, above) were prepared by mixing different natural products. The contents of all of the six NPs were not known to the microbiology team investigating them. All NPs were prepared freshly and stored in dark at 4° C. in the refrigerator.

Agar Well Diffusion Method A 0.5 McFarland suspension of each bacterial strain was prepared from a young growth (overnight incubation on blood agar plate) using sterile saline. For *Candida albicans* a 2.0 McFarland suspension was prepared. For the agar well diffusion test; a Mueller-Hinton agar plate (MHAP) was used. The whole surface of the MHAP was inoculated with the suspension of a microorganism. After sterilizing a cork borer in the flame of Bunsen burner, it was cooled; then was used to cut five wells in the MHAP. Two MHAPs were used for each microorganism. Each well was filled with an NP using a sterile pipette. One well was filled with fusidic acid ointment and another was filled with MEBO™ ointment. As a negative control, one well was filled with sterile water. The plates were covered and placed upside down in the incubator at 35° C. After an overnight incubation, the diameter of the clear zone around each well was measured three times and the average was recorded.

Sterility Testing of the NPs Using a sterile loop, a portion of each of the NPs was collected and inoculated on a blood agar plate (BAP) which was incubated aerobically at 35° C. for 48 hours. Another BAP was inoculated and incubated anaerobically at 35° C. for 72 hours. Also, a portion of each NP was inoculated in thioglycollate broth which was incubated at 35° C. for 24 hours, then, subcultured onto two BAPs, one was incubated aerobically and the other anaerobically at 35° C. for 48 hours.

Sterilizing the NPs Each NP was autoclaved with 15 pounds/square inch at 121° C. for 20 minutes. Sterility testing of the NPs was also performed after the autoclaving.

Broth Dilution Method For each of the NPs; four sterile test tubes were labeled as following; 100%, 50%, 25% and 12.5%. Using a sterile pipette, 1 ml of each NP was transferred into the 100% test tube (TT). A total of 1 ml of the nutrient broth was transferred into each of other TTs. Then, 1 ml of the tested NP was transferred into the 50% TT. After enough mixing, a total of 1 ml of the mixture was transferred into the next TT. Same procedures were repeated until the 12.5% TT, from which, after well mixing, a total of 1 ml was discarded. A microbial suspension of $5-6\times10^5$ CFU (colony-forming unit) was made for the tested microbial strain by transferring 1 ml of its 0.5 McFarland suspension into 9.0 ml of nutrient broth, after enough mixing, a total of 10 µl was inoculated into each of 100% to 12.5% TTs. A positive control was made by inoculating 10 µl of the microbial suspension into 1 ml of the nutrient broth. A negative control was made by adding 0.5 ml of the nutrient broth to 0.5 ml of the tested NP. For each TT, after well mixing, sub-culture was done immediately (i.e. at the 0.0 time), after 24 hours incubation (at 35° C.) and after 48 hours incubation (if growth was shown at 48 hours). Sub-culture was performed by taking a loopful of the culture medium and inoculating onto a fresh BAP. All BAPs were incubated at 35° C. aerobically for 24 hours. The minimum bactericidal concentration (MBC) was read as the least concentration showing no growth (on the sub-cultured BAPs) after 24 hours incubation of the TT. All tests were performed in triplicate and were repeated three times to obtain reliable results.

Results

Agar Well Diffusion Method The natural preparations NP0 and NP1 showed antibacterial effects on *Staphylococcus aureus* with 12 mm and 13 mm diameter of the clear zones respectively. No effects were observed on other microorganisms. Other NPs did not show any antimicrobial effects. It was noticed that bacterial and fungal (moulds) contaminants were growing from the wells filled with NPs if left more than 24 hours at room temperature.

Sterility Testing of the NPs The natural preparations NP0 and NP1 were contaminated with *Bacillus* spp. Other NP were contaminated with both *Bacillus* spp and fungal moulds.

Sterilizing the NPs Sterility tests of the NPs after the autoclaving showed that they were sterile.

Broth Dilution Method Antibacterial effects on *Staphylococcus aureus* showed that NP5 was the most effective as the 12.5% concentration was enough to kill the microorganism after 24 hours incubation. This was followed by NP2, NP3 and NP4 as the 50% concentration of each was effective to kill the microorganism after 48 hours incubation. For *Pseudomonas aerugenosa*, also NP5 was the most effective as the 12.5% concentration was enough to kill the microorganism after 24 hours incubation. This was followed by NP4 as the 12.5% concentration was enough to kill most of the microorganism with few colonies grown after 24 hours incubation and no bacterial growth after 48 hours incubation, Against *Enterococcus faecalis*, both NP4 and NP5 were the most effective as the 12.5% concentration of each was enough to kill the microorganism after 24 hours incubation. These were followed by NP2 and NP3 as the 25% concentration of each was effective to kill the microorganism after 24 hours incubation. For *Escherichia coli*, both NP4 and NP5 were the most effective as the 12.5% concentration of each was enough to kill most of the microorganism with few colonies grown after 24 hours incubation and no bacterial growth after 48 hours incubation. The 25% concentration of each of other NPs was enough to kill the microorganism after 24 hours incubation. For *Candida albicans*, NP5 was the most effective as the 25% concentration was enough to kill most of the microorganism with few colonies grown after 24 hours incubation and no fungal growth after 48 hours incubation. The 50% concentration of each of other NPs was effective to kill the microorganism after 24 hours incubation.

Discussion Each of the six natural preparations (NPs) showed antimicrobial activity against the microorganisms used in this study which include: *Staphylococcus aureus* (ATCC 29213), *Enterococcus faecalis* (ATCC 29212), *Pseudomonas aeruginosa* (ATCC 10145), *Escherichia coli* (ATCC 35218), *Candida albicans* (ATCC 60227). The most effective preparation was NP5 followed by NP4. The 25% concentration of NP5 was enough to kill all of the tested bacterial strains. Its 50% concentration was effective in killing *Candida albicans* after 24 hours incubation. Using the agar well diffusion method was not informative. The antimicrobial effect was not visible except with NP0. Each of other NPs did not show any clear effect. The reason for that could be due to the high viscosity of other NPs which prevents diffusion of the NP into the agar. Autoclaving was effective to kill all bacterial and fungal contaminants. It was clear that autoclaving did not destroy the antimicrobial activities of all of the NP.

Example 2

Effect of Some Natural Preparations on Bacteria Isolated from Infected Diabetic Foot Ulcers A controlled, blind comparative study to identify the organisms obtained from foot ulcers and to test effectiveness of NPs on the organisms.

List of the 11 agents used:
0. 100 g honey, 0 g myrrh, and 0 g black seed
1. 100 g honey, 1.25 g myrrh, and 0 g black seed
2. 100 g honey, 1.25 g myrrh, and 1.71 g black seed
3. 100 g honey, 2.5 g myrrh, and 1.71 g black seed
4. 100 g honey, 3.75 g myrrh, and 1.71 g black seed
5. 100 g honey, 5.0 g myrrh, and 1.71 g black seed
6. MEBO™
7. PUCIDIN™
8. Ciprofloxacylin
9. Clindamycin
10. Placebo Natural Preparations (NPs) Six NPs (NPs 0-5, above) were prepared by mixing different natural products. The contents of all of the six NPs were not known to the microbiology team investigating them. All NPs were prepared freshly and stored in dark at 4° C. in the refrigerator.

Clinical Microbial Strains Tissues (necrotic tissue/biopsy) and wound swabs were collected from three patients with infected diabetic feet admitted to the King Abdulaziz University Hospital (KAUH). All three patients were not on antimicrobial drugs for at least 3 days before collecting the specimens. The specimens were cultured in the Clinical Microbiology Laboratory at KAUH. A total of seven microorganisms were isolated from the three patients. Three microorganisms were isolated from the first patient (*Staphylococcus aureus*, an extended spectrum beta-lactamase(ESBL)-producer *Escherichia coli* and *Proteus mirabilis*). Two bacterial strains were isolated from the second patient (*Streptococcus pyogenes* and *Morganella morganii*). Another two strains were isolated from the third patient (a methicillin-resistant *Staphylococcus aureus* (MRSA) and *Streptococcus pyogenes*). Anaerobic microorganisms were not isolated from the three patients.

Sterility Testing of the NPs Using a sterile loop, a portion of each of the NPs was collected and inoculated on a blood agar plate (BAP) which was incubated aerobically at 35° C. for 48 hours. Another BAP was inoculated and incubated anaerobically at 35° C. for 72 hours. Also, a portion of each NP was inoculated in thioglycollate broth which was incubated at 35° C. for 24 hours, then, subcultured onto two BAPs, one was incubated aerobically and the other anaerobically at 35° C. for 48 hours.

Sterilizing the NPs Each of NP was autoclaved with 15 pounds/square inch at 121° C. for 20 minutes. Sterility testing of the NPs was also performed after the autoclaving.

Broth Dilution Method For each of the six NPs; four sterile test tubes were labeled as following; 100%, 50%, 25% and 12.5%. Using a sterile pipette, 1 ml of each NP was transferred into the 100% test tube (TT). A total of 1 ml of the nutrient broth was transferred into each of other TTs. Then, 1 ml of the tested NP was transferred into the 50% TT. After enough mixing, a total of 1 ml of the mixture was transferred into the next TT. Same procedures were repeated until the 12.5% TT, from which, after well mixing, a total of 1 ml was discarded. A microbial suspension of $5-6 \times 10^5$ CFU (colony-forming unit) was made for each clinical isolate by transferring 1 ml of its 0.5 McFarland suspension into 9.0 ml of nutrient broth, after enough mixing, a total of 10 µl was inoculated into each of 100% to 12.5% TTs. A positive control was made by inoculating 10 µl of the microbial suspension into 1 ml of the nutrient broth. A negative control was made by adding 0.5 ml of the nutrient broth to 0.5 ml of the tested NP. For each TT, after well mixing, sub-culture was done immediately (i.e. at the 0.0 time), after 24 hours incubation (at 35° C.) and after 48 hours incubation (if growth was shown at 48 hours). Sub-culture was performed by taking a loopful of the culture medium and inoculating onto a fresh BAP. All BAPs were incubated at 35° C. aerobically for 24 hours. The minimum bactericidal concentration (MBC) was read as the least concentration showing no growth (on the sub-cultured BAPs) after 24 hours incubation of the TT. All tests were performed in triplicate and were repeated three times to obtain reliable results.

Results

Sterility Testing of the NPs The natural preparations NP0 and NP1 were contaminated with *Bacillus* spp. Other NP were contaminated with both *Bacillus* spp and fungal moulds.

Sterilizing the NPs Sterility tests of the NPs after the autoclaving showed that they were sterile.

Broth Dilution Method For the microbial isolates of the first patient; the antibacterial effects on *Staphylococcus aureus* showed that NP5 and NP4 were the most effective as the 25% concentration of each was enough to kill the microorganism after 24 hours incubation. Other NPs were effective at 50% concentration. For the ESBL-producer *Escherichia coli*; all of the six NPs showed the same bactericidal effect at 25% concentration which was enough to kill the microorganism after 24 hours. For *Proteus mirabilis*; NP0 was the most effective as the 25% was enough to kill most of the microorganism with few colonies (1 colony) grown after 24 hours incubation and no bacterial growth after 48 hours incubation. The 50% concentration of each of the NPs was enough to kill the microorganism after 24 hours incubation. For the clinical isolates of the second patient; the antibacterial effects on *Streptococcus pyogenes* showed that NP5 was the most effective as the 12.5% concentration was enough to kill the microorganism after 24 hours incubation. All of the other NPs were effective at 25% concentration. For *Morganella morganii*; also NP5 was the most effective as the 12.5% concentration was enough to kill the microorganism after 24 hours incubation. All of the other NPs were effective at 25% concentration. For the bacterial isolates of the third patient; the antibacterial effects on MRSA showed that NP3 was the most effective as the 12.5% concentration was enough to kill most of the microorganism with few (5) colonies grown after 24 hours incubation and no bacterial growth after 48 hours incubation. The 25% concentration of each of the six NPs was enough to kill the microorganism after 24 hours incubation. For *Streptococcus pyogenes*; NP5 was the most effective as the 12.5% concentration was enough to kill the microorganism after 24 hours incubation. All of the other NPs were effective at 25% concentration except NP0 which required 50% concentration to kill the microorganism after 24 hours incubation.

Discussion Each of the six natural preparations (NPs) showed antimicrobial activity against each of the seven clinical strains isolated from the three patients with infected diabetic feet. The clinical isolates included; *Staphylococcus aureus*, an extended spectrum beta-lactamase-producer (ESBL-producer) *Escherichia coli* and *Proteus mirabilis* (from the first patient), *Streptococcus pyogenes* and *Morganella morganii* (from the second patient), methicillin-resistant *Staphylococcus aureus* (MRSA) and *Streptococcus pyogenes* (from the third patient). The most effective preparation was NP5 followed by NP4. The 12.5% concentration of NP5 was enough to kill *Streptococcus pyogenes* (two strains isolated from the second and the third patients) and *Morganella morganii*. The 25% concentration of NP5 was effective in killing *Staphylococcus aureus*, ESBL-producer *Escherichia coli* and MRSA. The natural preparation NP0 was the most effective NP against *Proteus mirabilis* as the 25% concentration was enough to kill most of the microorganism with only one colony grown after 24 hours incubation and no bacterial growth after 48 hours incubation. The 50% concentration of each of the six NPs was enough to kill the microorganism after 24 hours incubation. It seems that NP5 is the most effective preparation. The 50% concentration was bactericidal for all of the clinical isolates. Autoclaving was effective to kill all bacterial and fungal contaminants. It was clear that autoclaving did not destroy the antimicrobial activities of all of the NP. Antimicrobial-resistance of microorganisms is on rise, thus the discovery of alternative therapeutic agents is highly needed.

The invention claimed is:

1. A method for treating a wound infected with Methicillin-resistant *Staphylococcus aureus* (MRSA) in a subject in need thereof, comprising administering to the wound an effective amount of a composition comprising honey, myrrh, and *Nigella sativa* seeds.

2. The method of claim 1, wherein the wound is selected from the group consisting of bed sores and diabetic ulcers.

3. The method of claim 2, wherein the wound is a diabetic foot ulcer.

4. The method of claim 1, wherein the composition comprises honey:myrrh:*N. sativa* seed in a ratio of 100:0.5-50:0.1-10, based on weight.

5. The method of claim 1, wherein the composition comprises honey:myrrh:*N. sativa* seed in a ration of 100:6-7:1-1.5, based on weight.

6. The method of claim 1, wherein the composition comprises honey:myrrh:*N. sativa* seed in a ratio selected from the group consisting of 100:3.42:1.25, 100:5.13:1.25, 100:6.84:1.25, and 100:3.42:2.50, based on weight.

7. The method of claim 1, wherein the composition further comprises one or more pharmaceutically acceptable diluents and/or excipients.

8. The method of claim 1, wherein the composition further comprises wax.

9. The method of claim 8, wherein the composition comprises wax in an amount ranging from 1-50% by weight based on 100% by weight of the total composition.

10. The method of claim 8, wherein the composition comprises wax in an amount ranging from 15-25% by weight based on 100% by weight of the total composition.

11. The method of claim 1, wherein the composition is in the form of a gel.

12. The method of claim 1, wherein the composition is incorporated into a wound dressing.

* * * * *